United States Patent
Curry et al.

(10) Patent No.: US 7,057,185 B2
(45) Date of Patent: *Jun. 6, 2006

(54) MAXIMUM SENSITIVITY OPTICAL SCANNING SYSTEM

(75) Inventors: Bo U. Curry, Redwood City, CA (US); Andreas N. Dorsel, Menlo Park, CA (US); Kyle J. Schleifer, Los Gatos, CA (US); Debra A. Sillman, Los Altos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 10/910,552

(22) Filed: Aug. 2, 2004

(65) Prior Publication Data

US 2005/0061990 A1   Mar. 24, 2005

Related U.S. Application Data

(63) Continuation of application No. 10/087,619, filed on Feb. 28, 2002, now Pat. No. 6,870,166.

(51) Int. Cl.
*G01J 1/20* (2006.01)

(52) U.S. Cl. ............... 250/459.1; 250/458.1; 250/461.2

(58) Field of Classification Search ............. 250/459.1, 250/458.1, 252.1, 461.2; 356/371, 318, 417
See application file for complete search history.

(56) References Cited

U.S. PATENT DOCUMENTS

| | | | |
|---|---|---|---|
| 6,078,390 A | 6/2000 | Bengtsson | |
| 6,471,916 B1 | 10/2002 | Noblett | |
| 6,870,166 B1 * | 3/2005 | Curry et al. | 250/459.1 |

* cited by examiner

*Primary Examiner*—Otilia Gabor
*Assistant Examiner*—Christine Sung (57) ABSTRACT

A maximum sensitivity optical scanning system is disclosed. It finds use in a variety of applications, including the reading of biopolymeric arrays. It operates by scanning sample at a setting selected to result in signal saturation for some, but not all available data. Subsequent scans of the same area are taken at lower sensitivity settings (in terms of detector gain and/or excitation light source gain or attenuation) and data from at least the previously saturated regions is obtained. If system sensitivity is set too low to produce useful results, optional features may adjust sensitivity upward and follow with an increased sensitivity scan as a remedial measure. Full signal sensitivity is better preserved as most needed in taking data for the weakest signals first with the high-level scan. Data for sample producing stronger signals that can better tolerate photobleaching is then taken in one way or another.

33 Claims, 4 Drawing Sheets

MAXIMUM SENSITIVITY OPTICAL SCANNING SYSTEM

This application is a continuation and claims priority to application Ser. No. 10/087,619, filed Feb. 28, 2002 now U.S. Pat. No. 6,870,168, under 35 U.S.C. 120, the entirety of which is incorporated herein by reference.

FIELD OF THE INVENTION

This invention relates to optical scanners and, more particularly, to approaches for scanning low signal emission samples without photo-bleaching.

BACKGROUND OF THE INVENTION

Optical scanners find use in performing detection for various experiments, assays and the like. They are often used in array analysis systems for detection of surface bound binding complexes in genomic and proteomic applications. In fluorescence optical scanners, fluorescence emitted from a sample that has been excited by a light signal is collected and detected.

Often, a user has little idea of the brightness of the fluorescence that will be emitted by a particular sample. Accordingly, the user does not know a priori how high or low to set the attenuation of an attenuator that controls the optical excitation signal power, that is, the signal power that reaches the sample. Further, the user does not know how high or low to set the gain of a detector that collects emitted fluorescence and produces a corresponding data signal.

Previously known optical system setup techniques include manually setting the sensitivity of the system where a user adjusts both the gain of the fluorescence detector and attenuation of the excitation light source. Typically, the user scans a sample in raster fashion to locate an element in the micro-array that is known to contain a concentration of a fluorophore that should produce a maximum fluorescence in response to the excitation signal. The user then re-scans the portion of the sample that contains this element and iteratively adjusts the sensitivity of the system until, in the judgment of the user, the corresponding data signal is sufficiently close to a maximum data signal value of the system. If the system has two channels, that is, produces excitation signals using two lasers of different wavelengths, the user re-scans the sample using the signal produced by the second laser and repeats the iterative, manual adjustment process to determine the appropriate sensitivity settings for the second channel. A user would further re-scan the sample for each additional channel.

The adjustment ranges of the attenuator or excitation source power and the detector are relatively large. Accordingly, manual adjustment of these components is time consuming, particularly since adjustment of either one of them may require a re-adjustment of the other. Thus, with manual scanning, the sample may be scanned many times to set the sensitivity of, or calibrate, the system. When multiple channels are used, more time is spent manually calibrating the system and the sample is scanned even more times, as discussed above.

If the excitation power and/or attenuator gain are set too low (i.e., detector sensitivity is too far reduced), the system may not accurately distinguish between different lower levels of emitted fluorescence. If the excitation signal power and/or detector gain are set too high, the system saturates. As stated in U.S. Pat. No. 6,078,390 to Bengtsson, assigned to General Scanning, Inc. (Watertown, Mass.), the general view is that such saturation results in a failure to make accurate measurements.

In response to such difficulties, the Bengtsson patent describes a scanning system and method of operation for automatically setting detection sensitivity. It employs an optical scanning system using a low-resolution scanning operation to automatically adjust the sensitivity of the system. The system performs a low-resolution scanning operation by scanning a line, automatically and iteratively setting the levels of excitation signal power and detector gain, skipping a plurality of lines and scanning a next line, adjusting the levels as appropriate, skipping a plurality of lines and scanning a next line, and so forth. After the system sensitivities have been set, the calibrated system then scans all the lines of the sample to collect data. The calibrated system thus scans for the first time the lines that were skipped during the low resolution "calibration" scanning operation.

For these skipped lines, photo-bleaching (i.e., weakening of fluorescent signal caused by exposure to excitation light) is avoided. With the other lines, however, the same problems encountered with manual scanning and tuning optical system attenuation or excitation system gain from photo-bleaching as a result of rescanning are encountered. The risk of damage to the sample is further increased when multiple channels are used.

SUMMARY OF THE INVENTION

The system of the present invention handles the reality of photobleaching in a different fashion. Rather than scanning samples and adjusting system limits to avoid photobleaching of unscanned samples during detection steps as in the Bengtsson patent, the present invention acquires valid data from some sample while the signal associated with other data is saturated. In this manner, low value signals are accurately detected with greatest accuracy. Rescanning areas producing more intense signals for detection after exposure resulting in photobleaching is not problematic since the relatively higher signal strength enables adequate data acquisition despite the deleterious effect of repeated light exposure.

The present invention handles issues associated with sensor saturation and photobleaching—not by seeking to eliminate each to the fullest extent possible, but by working around the problems they represent. Accordingly, the approach of the present invention is believed to offer improvement in detection accuracy in an elegant system. Furthermore, the invention accomplishes its goal in a highly time-efficient manner, saving resources in that regard. Additional benefits and advantages may also be apparent to those with skill in the art reviewing the subject disclosure.

The present invention is a maximum sensitivity optical scanning system. Generally, it operates by scanning a sample, such as in a DNA micro-array, at a setting calculated to result in signal saturation for some, but not all, available data. Preferably, scanning is accomplished at a maximum setting for a given scanning apparatus so that the weakest signal possibly detected may be observed. Sometimes complete signal saturation may result. This condition indicates that no weak data is present. Whether or not data for weak signals is detected, one or more subsequent scans of the same area are taken at lower settings (in terms of detector attenuation and/or excitation light source gain) and data from at least those previously saturated regions is obtained.

This methodology works to preserve full signal sensitivity in taking data for the weakest signals. Another aspect of the invention provides for upward adjustment of scanning sensitivity, especially to obtain results when indication is received that a decreased sensitivity scan did not yield sufficiently strong results. Further, hardware associated with the methodology and programming optionally used to carry out the methods are part of the present invention. The system of the invention may incorporate known hardware as described herein or be otherwise implemented.

DETAILED DESCRIPTION OF THE INVENTION

In describing the invention in greater detail than provided in the Summary of the Invention above, suitable hardware for use with the invention is first described, followed by the subject methodology or algorithm(s). Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Furthermore, where a range of values is provided, it is understood that every intervening value, between the upper and lower limit of that range and any other stated or intervening value in that stated range is encompassed within the invention. The upper and lower limits of these smaller ranges may independently be included in the smaller ranges as encompassed by the invention, subject to any specifically excluded limit in the stated range. Where the stated range includes one or both of the limits, ranges excluding either or both of those included limits are also included in the invention. Also, it is contemplated that any optional feature of the inventive variations described herein may be set forth and claimed independently, or in combination with any one or more of the features described herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All existing subject matter mentioned herein (e.g., publications, patents, patent applications and hardware) is incorporated by reference herein in its entirety. The referenced items are provided solely for their disclosure prior to the filing date of the present application. Nothing herein is to be construed as an admission that the present invention is not entitled to antedate such material by virtue of prior invention.

It is noted that as used herein and in the appended claims, the singular forms "a", "and", "said" and "the" include plural referents unless the context clearly dictates otherwise.

It is further noted that the claims may be so drafted to exclude any optional element. As such, this statement is intended to serve as antecedent basis for use of such exclusive terminology as "solely," "only" and the like in connection with the recitation of claim elements or use of a "negative" limitation.

Figure 1:
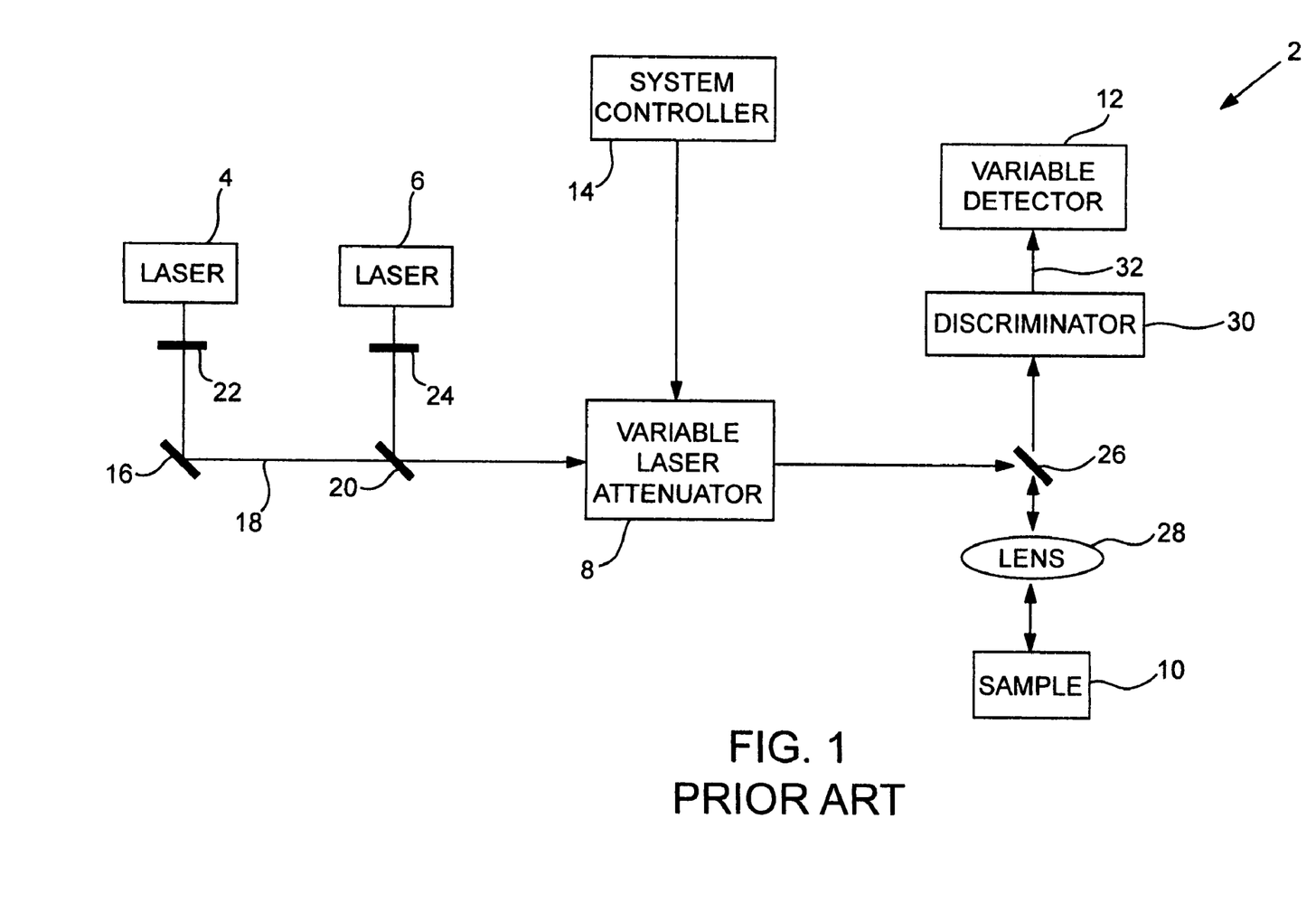
FIGS. 1 and 2 are functional block diagrams of optical scanning systems that may be used in the present invention.

Turning now to the figures, FIG. 1 shows an optical detection system as shown and described in the Bengtsson patent referenced above. While the present invention utilizes a different approach to scanning, it may use identical hardware as is known in the art. The optical scanning system 2 shown includes two lasers 4 and 6, a variable laser attenuator 8 that controls the excitation signal power that is delivered to a sample 10, and a variable gain detector 12 that receives fluorescence emitted from the sample and produces associated data signals. As discussed in more detail below, a system controller 14 including a computer or data processor controls the attenuator 8 and the detector 12, to set the sensitivity of the system according to the methodology described.

Scanning operations that use, for example, the excitation signal produced by the laser 4 are over a first channel, and scanning operations that use the excitation signal produced by the laser 6 are over a second channel. The term "channel" refers essentially to the system configured appropriately for the particular excitation signal, such as, for example, the selection of or conditioning of filters to pass or reject signals of the appropriate wavelengths and, as discussed in more detail below, the settings of appropriate levels of detector gain and attenuation levels. The drawing depicts two lasers, however, a single laser or a greater number of lasers may be included in the system with scanning operations over a corresponding number of channels, as appropriate for a particular application. Further, alternative excitation signal sources, such as, for example, xenon lamps or light-emitting-diodes, may be used instead of the lasers.

The variable attenuator 8 may be, for example, an addressable array of selected neutral fixed-density filters; a continuously variable neutral density filter; a plurality of polarizers that includes at least one rotatable polarizer; or a rotating polarization retarder placed in front of a polarizer, all of which are known in the art. Alternatively, attenuator 8 may be omitted in favor of directly controlling the power of the excitation signal source. Such direct control may be accomplished using controller 14 to vary the voltage and/or amplitude of a signal dictating the operation of the excitation signal source. Typically, laser power has a generally linear relationship to input voltage that is easily determined and applied to control excitation source power output or gain.

As shown, mirror 16 may direct a beam 18 from laser 4 to a beam combiner 20, which transmits light at the wavelength produced by the laser 4 and reflects light at the wavelength produced by the laser 6. Beam combiner 20 may be, for example, a dichroic filter with thin-film interference coatings that transmit and reflect light at the respective wavelengths. It may be used to combine the beams from the two lasers into a single, collimated beam.

Shutters 22 and 24 may be provided and operated in a conventional manner to control the passing of light from the lasers to the beam combiner, such that at any given time light from only one laser reaches the beam combiner. Beam combiner 20 will then pass or reflect the beams, as appropriate. The beam combiner thus ensures that the beam from each laser travels along the same path to the sample 10.

A single or combined beam 18 may next pass through attenuator 8, resulting in an attenuated, collimated beam with a desired power level. Of course, the positions of any attenuator and beam combiner provided may be reversed, with the beam combiner passing, reflecting or combining the attenuated beams.

Preferably, a beam splitter 26 reflects the beam through a lens or lens assembly 28. The lens assembly focuses the beam and directs it to the sample 10. Beam splitter 26 also transmits light that lens assembly 28 collects from the sample 10 to variable gain detector 12.

Lens assembly 28, may be similar to a conventional microscope objective lens assembly, including multiple elements (not shown) that are mounted in a metal cell. Preferably, the lens assembly has a large working distance, a limited chromatic correction range and includes an objective lens with a high numerical aperture.

However configured (as would be a matter of routine design choice), lens assembly 28 focuses the combined, collimated beam that it receives to a spot that (for a micro-array scanner) is often within the range of approximately 1 to 20 microns in diameter measured at the full-width half-maximum point. Of course, the lens assembly may produce a light spot with a larger diameter when the sample includes relatively large targets, or dots.

In response to the light spot, fluorescent chemical tags in the sample emit fluorescent light that is typically at a longer wavelength than the impinging light. Lens assembly 28 collects a portion of the emitted fluorescent light. It collimates and focuses the collected fluorescent light and directs it to a fluorescence emission wavelength discriminator 30. Discriminator 30 preferably operates in a conventional manner to filter the light from the sample. The discriminator, at any given time, passes light at a desired peak fluorescence wavelength and rejects light at other wavelengths, including light from the sample excitation sources that may be reflected from the sample 10. The discriminator may be, for example, an arrangement of emission filters that pass a desired narrow spectrum of fluorescent light. Alternatively, the discriminator may be a prism or grating that likewise passes the narrow spectrum of fluorescent light.

Discriminator 30 passes fluorescent light 32 to variable gain detector 12, which may be, for example, a photomultiplier tube (PMT) detector, a photodiode, a charge coupled device (CCD) or comprise other suitable hardware. Detector 12 preferably then sends data signals relating to the fluorescent light to the system controller 14, which records them for later use.

System 2 may include a plurality of discriminators in the path of the collimated fluorescent light, and a plurality of detectors. In which case, each discriminator will direct fluorescent light of a desired wavelength to an associated detector, and reject other wavelengths. The detectors can then each be matched specifically to a particular wavelength, and scanning operations involving multiple wavelengths can easily be performed simultaneously. Further, such a setup will avoid the need for shutters 22 and 24, or allow the system to be operated in synchronism to pass the multiple wavelengths.

Figure 2:
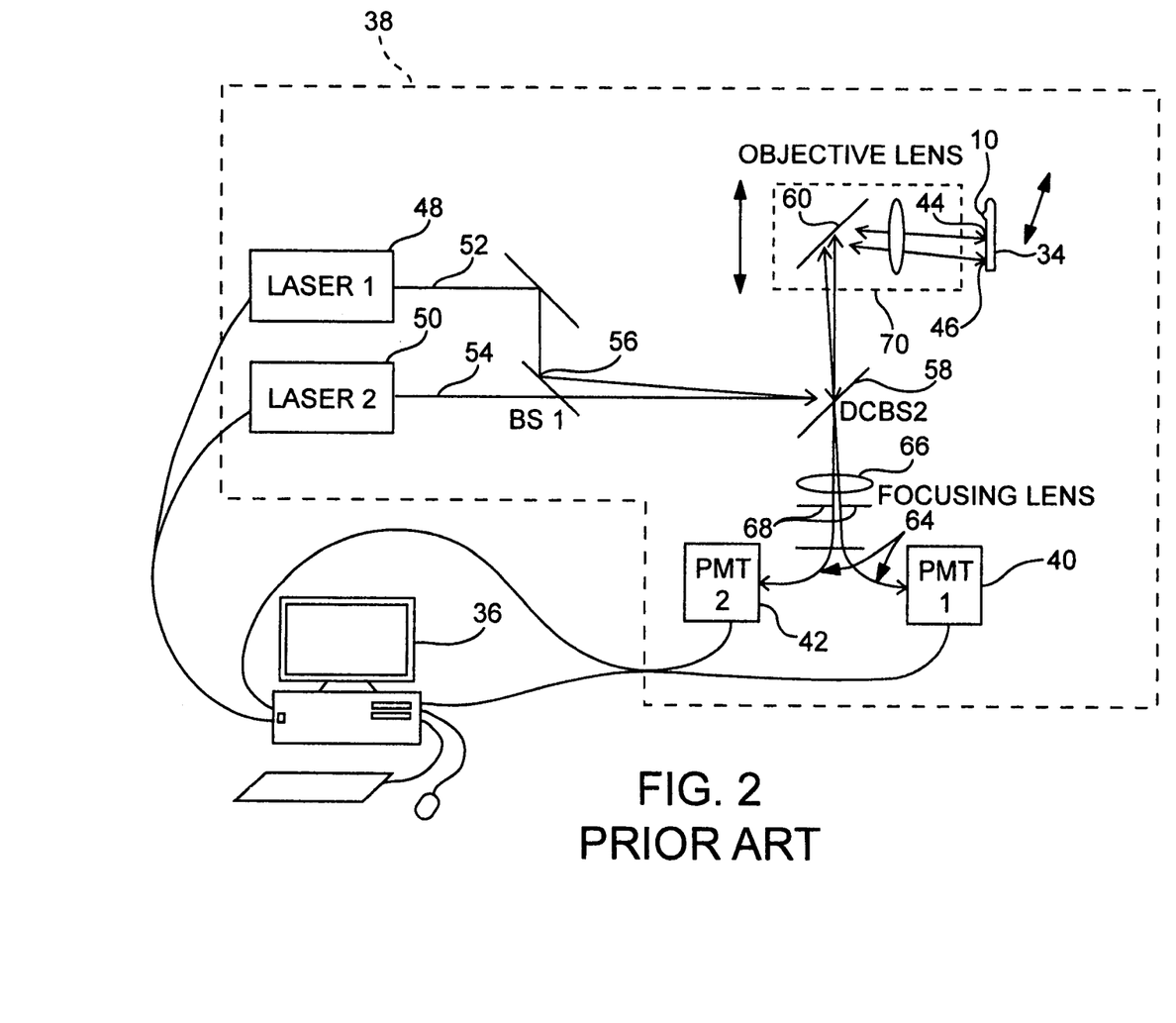

Other hardware may also be used in connection with the present invention. For instance, the hardware described in U.S. Pat. Nos. 5,091,652; 5,294,799, U.S. patent application Ser. No. 09/846125, titled "Reading Multi-Featured Arrays" and Ser. No. 09/430214, titled "Interrogating Multi-Featured Arrays" each to Dorsel et al., a Hewlett-Packard G2500A system or an Agilent Microarray Scanner system may be used. It may be most preferred to use a system as shown in FIG. 2 and described in U.S. Pat. No. 6,320,196 to Dorsel, et al. in connection with the present invention.

FIG. 2 shows a confocal instrument system that allows an operator to simultaneously scan the multifrequency wavelength emission from two separated spots on a sample 10 labeled with two dyes and supported on a sample substrate 34. A computer 36 with included processor, controls a laser induced fluorescence scanner 38. Detectors 40 and 42 measure the emission resulting from two spots 44 and 46.

This hardware variation preferably includes two lasers, 48 and 50 which generate laser beams 52 and 54 of different wavelengths for exciting the two spots on sample substrate 34. The laser beams are combined by passing them through a first (dichroic) beam splitter 56 at a slight angle (the illustration is exaggerated for clarity) and reflected off a dichroic beam splitter 58. The laser beams are redirected by a folding mirror 60 and focused by an objective lens or lens assembly 62 onto the two separate spots 44 and 46. Fluorescent light emission from the spots is imaged back through objective lens 62 and fold mirror 60, through dichroic beam splitter 58 for imaging onto two multi-mode (or in other instances monomode) fibers 64 by a focusing lens or lens assembly 66. Fibers 64, one for each of the two spot's images, serve as a pinholes and also guide the fluorescent light emission to two respective detectors 40 and 42. In the preferred embodiment, the detectors comprise PMTs, but other devices such as an avalanche photo diode, a photo diode or a CCD may be employed. Detectors 40 and 42 may optionally contain a (compound) lens for imaging the light from the fiber onto the detector, as well as a filter for controlling the portion of the spectrum that is actually detected. The scanner may further include polarizers 68 each in a corresponding detection path.

In a typical arrangement, a "chip" for supporting a sample is used. The chip may be scanned by moving the scan lens and fold mirror assembly 70 back and forth across in one dimension, and slowly moving the chip in the orthogonal direction to produce a two dimensional scan. Alternately, relative motion of sample and confocal scanning spots can be achieved using a substrate carrier that is set into a spinning motion by a motor upon which the substrate is eccentrically mounted. The spindle carrier can be designed to carry more than one substrate in order to improve duty cycle. The spinning motion can be constant angular velocity or can be varied such that the linear velocity across the chip is independent of the radius of the scanning circle. (This radius may differ slightly for the two beams if they are offset other than tangentially, but this should typically only cause higher order effects.) While the spinning motion provides for a mostly tangential scanning motion, mostly radial scanning can be achieved by moving the motor with the substrate carrier, (e.g., using a translation stage). Preferably, the spinning motion would be the fast scanning motion and the translation the slow scanning motion such that the spots move across the substrate in a spiral trace.

A modification obvious to someone skilled in the art would be to slowly move the lens assembly radially. In this case, a polarizer is introduced into each of the detection paths, the crosstalk between which is to be reduced by polarization. The polarizer is then oriented in such a way as to maximize transmission of the (partially) polarized emission to be detected in the channel in question. For an eccentric (rectangular) sample substrate, the scanner will only receive signal intermittently. For a larger, concentric (round) substrate one would get a continuous signal while scanning an annular area on the substrate.

Furthermore, as with the system in FIG. 1 described above, the order of the components may be changed or modified by one of ordinary skill in the art. For example, an optical system comprising a dichroic beam splitter for first splitting the fluorescent light into two channels, lenses (with possibly less demanding chromatic correction) for focusing the light of these two channels into two pinholes/fibers, wherein the fibers guide the light to PMT's with or without additional converging/collimating/imaging lenses may be employed. As another example, the first dichroic used above to combine the two laser beams can be replaced with a mirror because the beams may be spatially separated due to their tilt.

However configured, the design described in FIG. 2 is particularly effective in providing for low limit detection and ratio determination of two dye channels over a wide dynamic range. The invention also provides for two dye simultaneous reading and deconvolution (option for four dyes in simultaneous scans).

Figure 3A:
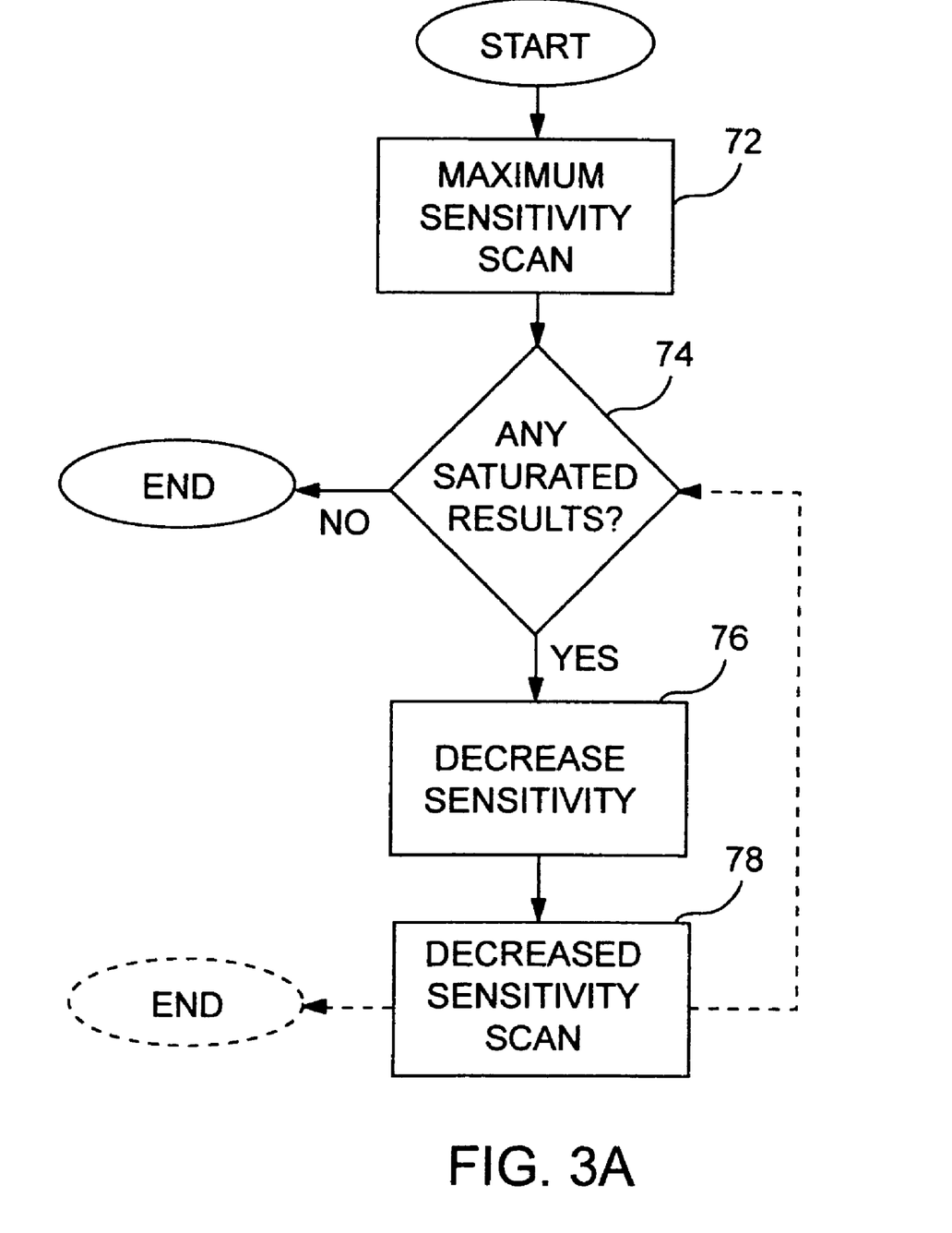
FIGS. 3A and 3B are flow charts illustrating the operation of the invention.
Figure 3B:
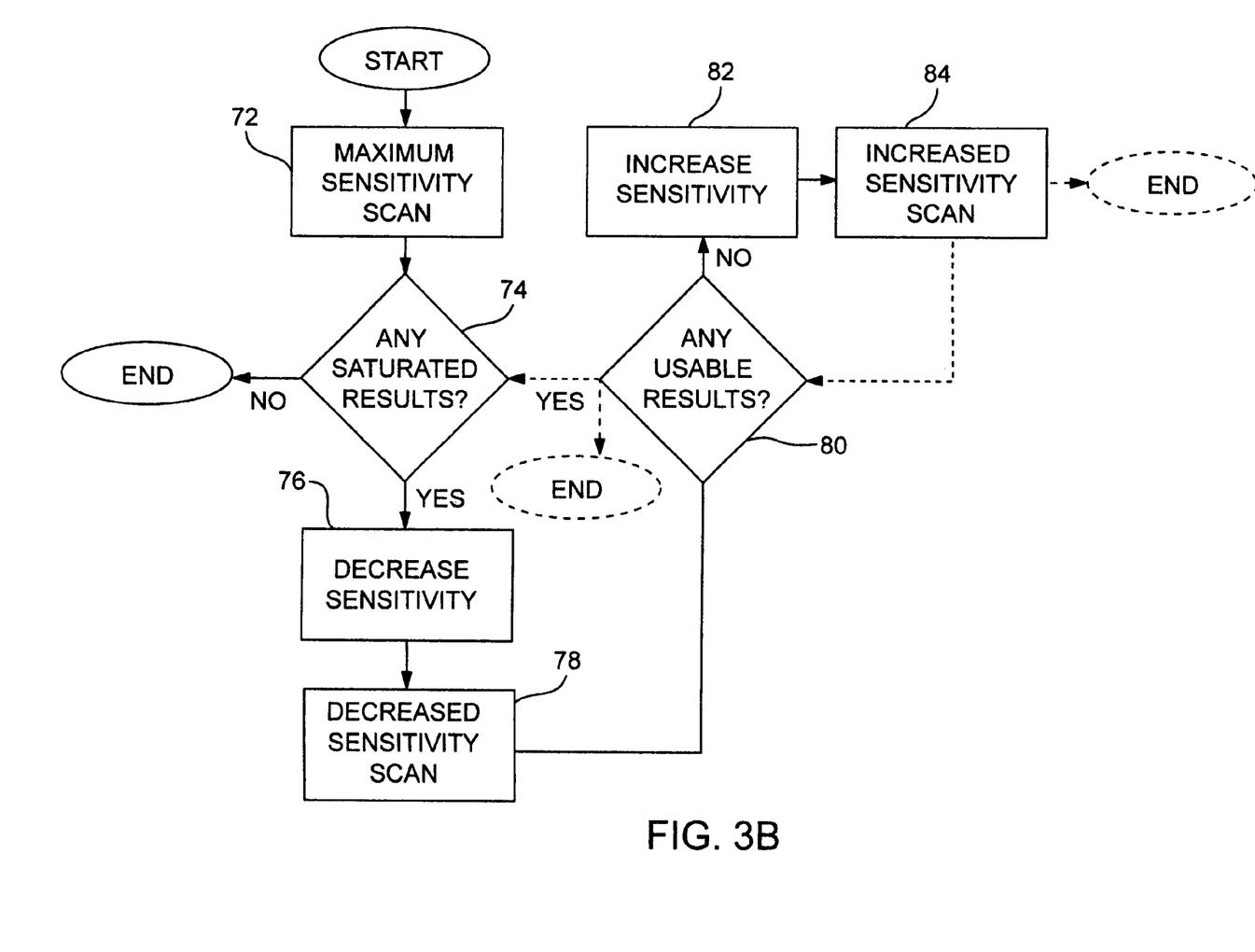

Whatever the hardware used (whether that shown in FIG. 1 or 2, a combination of the features, a further-modified device, or otherwise), the methodology described in connection with FIGS. 3A and 3B is preferably programmed into controller 14, computer 36 or other electronic control means to operate the hardware and create a system according to the present invention. The program may be provided in connection with a computer-readable medium such as a CD, DVD, hard disk, floppy disk, RAM, "hard-wired" logic, etc.

According to the methodology of the present invention, (whether using single or multiple light spots or multiple channels), a first automatic scan 72 of a site is made. When possible in view of the hardware selected, scanning for multiple channels and/or light spots is preferably accomplished simultaneously. However, with hardware configurations in which this is not possible, rather than running a full set of scans for each color or channel as described further below, the process will preferably proceed with highest intensity scans for each channel being made first, followed by any decreased sensitivity scans made in a turn-based manner (i.e., first a decision, adjustment or scan is made for one channel at a given point in the process followed by similar action for other channel(s) at that same point in the process, etc.). In systems with completely uncoupled channels, such that scanning in one channel does not photobleach or otherwise compromise the signal in other channels, it may be acceptable to run through the whole process as described below for each channel sequentially. Whatever the case, for the sake of clarity as the invention is explained further below, it will be made in the context of a single channel system, though the plurality of scans called for in connection with multiple channels may be implied.

The first scan (or set of scans) will typically be at full-power scan (i.e., a scan taken at the limits of detector attenuation or gain and excitation source power). In this way, the scan is taken at the maximum system sensitivity.

It is possible, however, that the initial scan setting might be set below the system sensitivity limit. When it is known a priori that no weak signals are present or likely to be present (for instance by related experiments), excitation source gain or attenuation and/or detector gain may be set lower so the results of the first automated scan are, hopefully, not completely saturated. Generally, the initial scan made automatically by the system is to be the highest sensitivity level scan—and thus, the "maximum" sensitivity scan—made according to the inventive algorithm.

After the initial scan, system logic preferably performs a check 74 to determine if any of the scanned area resulted in saturated readings. If no "results" are saturated, then the first scan is the only scan and the scanning process ends as illustrated. At the end point, scanning ceases and the data obtained is processed and/or displayed as typically done in the art.

By "results," it is preferably meant information from statistically relevant pixel(s). When scanning is accomplished, a PMT or CCD image obtained is represented by a number of pixels. Some of those pixels may show up as saturated regardless of the amount of sample in the region being scanned. A smudge, lint or other contaminant may be the cause, as may faulty hardware. Such readings are typically discarded upon operation of analytical techniques commonly practiced in the optical acquisition of data before check 74. Examples of such techniques are described in John C. Russ, "The Image Processing Handbook," Chapter 3, 3rd Edition (1998), and/or embodied in optical scanner instruments such as the AGILENT MICROARRAY SCANNER (product no. G2565AA) available from Agilent Technologies, Palo Alto, Calif. and biological image-processing tool kits such as BioImage, see the "www" site of "mih.unib-as.ch/Bioimage/Consortium/BItools.html." Pixels that are not statistically selected or otherwise modified—as in median filtering—may, however be counted as "results" in less preferred variations of the invention.

If a check procedure is included and some of the results thus defined are saturated, then system sensitivity is decreased as shown at step 76. Even without checking, however, the system could proceed to decrease sensitivity for another scan. Still, without check 74, significant advantages in terms of time savings and scanning accuracy may be lost.

The manner in which system sensitivity is decreased may vary. In general, the decrease may be related in some way to the amount or extent of result saturation. More complete result saturation will indicate the need for a more dramatic decrease in sensitivity. Either one or both of the gain of the light source(s) or detector(s) (e.g., PMT, CCD, etc.) may be changed to allow rescanning at a reduced scale factor. The decrease in sensitivity applied to the system may be a drop in light source power reaching the sample, detector gain or both. In the case of PMT sensitivity, while the relation between applied voltage and gain is nonlinear, the extent of change may be predicted utilizing the power law published by hardware vendors with empirically determined coefficients to make an estimate or by an iterative approach in testing gain obtained in varying voltage against expected results. Typically, sensitivity will be reduced by a scale factor between about 2 and 10 times. Still, more drastic modifications are possible, even if some commercially available scanning systems are not set up to accommodate such input.

Once system sensitivity is adjusted, a decreased sensitivity scan 78 is performed. One option is for the process to simply terminate at this point. Another option is that a second decision 74 is made resulting in process termination if no saturated results are detected, or proceeding again to decrease resolution and perform another decreased resolution scan.

FIG. 3B shows another variation of the invention adding functionality to the algorithm represented by FIG. 3A. Here, another decision 80 is made based on whether useable results are obtained from the decreased sensitivity scan 78. Especially where a heuristic-type approach as described above is not applied to decrease system sensitivity, it may be possible that sensitivity is decreased to a point where no usable results are produced or register. However, in normal operation, this will not usually occur. In the event that sufficient results are produced by scan 78, one of two occurrences may follow. A first option is that the process ends. A second option is that the process proceeds to check for any saturated results again according to feature 74 and feed into the method(s) described above.

In the event sufficient or useable results are not produced, a system sensitivity increase 82 is made. An increased sensitivity scan 84 follows. The process may end there or next proceed to check for usable results again.

As with the manner in which system sensitivity can be decreased, the manner in which it is increased may vary. Generally, the magnitude of the increase should be less than decrease that produced no usable results. The increase in system sensitivity may be on the order of about one-half of the preceding system sensitivity decrease.

Of course, upon review of either approach taught in FIGS. 3A and 3B, it will be apparent that multiple decreased or increased sensitivity scans might be made according to the results obtained. In order to best preserve sample from photobleaching in the event further scanning is in order, when increasing or decreasing system sensitivity it is preferred to set detector sensitivity at maximum or at higher levels and minimize the power of the light source reaching the sample. With a well-tuned system or approach, however, a single high sensitivity scan followed by a single decreased sensitivity scan will be needed to obtain adequate results. Still, the flexibility offered with the additional algorithm features is valuable in itself. In some instances, it may be preferred that a system according to the present invention be configured to allow selection between any of the options described.

For a second and any subsequent reduced-sensitivity or increased sensitivity scans, correction for the results of the (known, calibrated) effects of photobleaching from preceding scans (at least the first, maximum sensitivity scan) is preferably applied. What is more, additional steps or actions may be made in connection with or intermediate to the actions disclosed. However, for the sake of speed and economy, the invention is preferably practiced with only with such primary activities as shown in the figures and any associated data correction and/or filtering.

EXAMPLE

The present invention is preferably used in conjunction with arrays of polymeric binding agents spotted onto a surface—possibly by ink-jet printheads, by pin spotting or otherwise. The arrays will usually include at least two distinct polymers that differ by monomeric sequence immobilized on, e.g., covalently or non-covalently attached to, different and known locations on the substrate surface. Each distinct polymeric sequence of the array is typically present as a composition of multiple copies of the polymer on the substrate surface, e.g. as a spot on the surface of the substrate. The number of distinct polymeric sequences, and hence spots or similar structures, present on the array may vary, but is generally at least 2, usually at least 5 and more usually at least 10, where the number of different spots on the array may be as a high as 50, 100, 500, 1000, 10,000 or higher, depending on the intended use of the array. The spots of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like. The density of spots present on the array surface may vary, but will generally be at least about 10 and usually at least about 100 spots/cm2, where the density may be as high as 106 or higher, but will generally not exceed about 105 spots/cm$^2$.

In the broadest sense, the preferred arrays are arrays of polymeric binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini, e.g. the 3' or 5' terminus. Sometimes, the arrays are arrays of polypeptides, e.g., proteins or fragments thereof.

The subject arrays find use in a variety applications, where such applications are generally analyte detection applications in which the presence of a particular analyte in a given sample may be detected qualitatively or quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface.

The presence of this binding complex on the array surface is detected according to the present invention by optical means, e.g. through the use of fluorescent label present on the analyte, detecting chemiluminescent or electroluminescent labels or otherwise. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system.

Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the arrays are arrays of polypeptide binding agents, e.g., protein arrays, specific applications of interest include analyte detection/proteomics applications, including those described in: U.S. Pat. Nos. 4,591,570; 5,171,695; 5,436,170; 5,486,452; 5,532,128; and 6,197,599; the disclosures of which are herein incorporated by reference; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

The subject methods may include an act of transmitting data or results from at least one of the detecting and/or deriving acts, to a remote location. By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc. Results according to the present invention (including further processing such as accounting for photobleaching or not) may be forwarded (such as by communication) to a remote location if desired, and received there for further use (such as processing or further processing).

CLAIMS

Though the invention has been described in reference to certain examples, optionally incorporating various features, the invention is not to be limited to the set-ups described. The invention is not limited to the uses noted or by way of the exemplary description provided herein. It is to be understood that the breadth of the present invention is to be limited only by the literal or equitable scope of the following claims.

That being said, we claim:

1. A method comprising:
performing a first automated scan of a sample contacted array, wherein at least some results of said scan are saturated to obtain a first set of non-saturated results; and
performing a second automated scan of said sample contacted array at a decreased sensitivity from said first scan to obtain a second set of non-saturated results.

2. The method of claim 1, wherein said first scan is performed at a scanning system maximum sensitivity.

3. The method of claim 1, wherein said second scan is performed with a sensitivity decreased between about 2 and 10 times that of said first scan.

4. The method of claim 1, further comprising:
determining if results from said first automated scan are saturated.

5. The method of claim 1, further comprising:
determining if results from said second automated scan are saturated.

6. The method of claim 1, further comprising:
performing a third automated scan with sensitivity decreased from said second scan.

7. The method of claim 6, further comprising:
determining if results from said third automated scan are saturated.

8. The method of claim 1, further comprising:
performing a third automated scan with sensitivity increased from said second scan, wherein said sensitivity is lower than that of said first scan.

9. The method of claim 8, further comprising:
determining if results from said third automated scan are saturated.

10. The method of claim 8, further comprising:
performing a fourth automated scan with a sensitivity increased from said third scan, wherein said sensitivity is lower than that of said first scan.

11. The method of claim 8, further comprising:
performing a fourth automated scan with a sensitivity decreased from said third scan, wherein said sensitivity is higher than that of said second scan.

12. The method of claim 1, wherein said array is a biopolymer array.

13. The method according to claim 12, wherein the biopolymer is selected from the group consisting of polypeptides and nucleic acids.

14. The method of claim 1, further comprising:
transmitting results obtained by said optical scanning from a first location to a second location.

15. The method of claim 14, where said second location is a remote location.

16. A method comprising:
performing a first automated scan of a sample contacted array;
determining if any results from said first scan are saturated; and
terminating scanning if no results are saturated, or performing a second automated scan of said sample contacted array at a decreased sensitivity from said first scan If any results are saturated.

17. The method of claim 16, wherein said first scan is performed at a scanning system maximum sensitivity.

18. The method of claim 16, wherein said second scan is performed with a sensitivity decreased between about 2 and 10 times that of said first scan.

19. The method of claim 16, further comprising:
determining if results from said second automated scan are saturated.

20. The method of claim 16, further comprising:
performing a third automated scan with sensitivity decreased from said second scan.

21. The method of claim 20, further comprising:
determining if results from said third automated scan are saturated.

22. The method of claim 16, further comprising:
performing a third automated scan with sensitivity increased from said second scan, wherein said sensitivity is lower than that of said first scan.

23. The method of claim 22, further comprising:
determining if results from said third automated scan are saturated.

24. The method of claim 22, further comprising:
performing a fourth automated scan with a sensitivity increased from said third scan, wherein said sensitivity is lower than that of said first scan.

25. The method of claim 22, further comprising:
performing a fourth automated scan with a sensitivity decreased from said third scan, wherein said sensitivity is higher than that of said second scan.

26. The method of claim 16, wherein said array is a biopolymer array.

27. The method according to claim 26, wherein the biopolymer is selected from the group consisting of polypeptides and nucleic acids.

28. The method of claim 16, further comprising:
transmitting results obtained by said optical scanning from a first location to a second location.

29. The method of claim 28, where said second location is a remote location.

30. A system programmed to operate according to a method comprising: performing a first automated scan of a sample contacted array;
determining if any results from said first scan are saturated; and
terminating scanning if no results are saturated, or performing a second automated scan of said sample contacted array at a decreased sensitivity from said first scan if any results are saturated.

31. The system of claim 30 comprising at least one light excitation source and at least one fluorescence detector.

32. A computer-readable medium embodying a program to direct a machine to perform a method comprising:
performing a first automated scan of a sample contacted array;
determining if any results from said first scan are saturated; and
terminating scanning if no results are saturated, or performing a second automated scan of said sample contacted array at a decreased sensitivity from said first scan if any results are saturated.

33. A computer-readable medium containing data representing sample results, wherein said data is made by a method comprising:
performing a first automated scan of a sample contacted array;
determining if any results from said first scan are saturated; and
terminating scanning if no results are saturated, or performing a second automated scan of said sample contacted array at a decreased sensitivity from said first scan if any results are saturated.

* * * * *

UNITED STATES PATENT AND TRADEMARK OFFICE
CERTIFICATE OF CORRECTION

PATENT NO. : 7,057,185 B2
APPLICATION NO. : 10/910552
DATED : June 6, 2006
INVENTOR(S) : Curry et al.

Page 1 of 1

It is certified that error appears in the above-identified patent and that said Letters Patent is hereby corrected as shown below:

On the title page, in item (56), under "U.S. Patent Documents", in column 2, line 3, after "6,870,166" delete "B1" and insert -- B2 --, therefor.

Column 12, line 37, in Claim 16, delete "If" and insert -- if --, therefor.

Signed and Sealed this

Fifth Day of December, 2006

JON W. DUDAS
*Director of the United States Patent and Trademark Office*